US011701028B2

(12) United States Patent
Ricci et al.

(10) Patent No.: US 11,701,028 B2
(45) Date of Patent: Jul. 18, 2023

(54) SYSTEM FOR PROCESSING RESPIRATORY RATE

(71) Applicant: Murata Vios, Inc., Woodbury, MN (US)

(72) Inventors: Carlos A. Ricci, Apple Valley, MN (US); Vladimir V. Kovtun, Inver Grove Heights, MN (US); Scott Thomas Mazar, Woodbury, MN (US)

(73) Assignee: VIOS MEDICAL, INC., Woodbury, MN (US)

( * ) Notice: Subject to any disclaimer, the term of this patent is extended or adjusted under 35 U.S.C. 154(b) by 366 days.

(21) Appl. No.: 16/922,616

(22) Filed: Jul. 7, 2020

(65) Prior Publication Data

US 2021/0038115 A1    Feb. 11, 2021

Related U.S. Application Data

(60) Provisional application No. 62/883,339, filed on Aug. 6, 2019.

(51) Int. Cl.
*A61B 5/08* (2006.01)
*A61B 5/00* (2006.01)
*A61B 5/085* (2006.01)

(52) U.S. Cl.
CPC .......... *A61B 5/0816* (2013.01); *A61B 5/0803* (2013.01); *A61B 5/085* (2013.01);
(Continued)

(58) Field of Classification Search
CPC ..... A61B 5/083; A61B 5/7225; A61B 5/7203; A61B 5/7235; A61B 5/0809;
(Continued)

(56) References Cited

U.S. PATENT DOCUMENTS 7,702,502 B2   4/2010   Ricci et al.
7,706,992 B2   4/2010   Ricci et al.
(Continued)

OTHER PUBLICATIONS

Cooley, W. L., & Longini, R. L. (1968). A new design for an impedance pneumograph. Journal of Applied Physiology, 25(4), 429-432. https://doi.org/10.1152/jappl.1968.25.4.429 (Year: 1968).*

*Primary Examiner* — Eric F Winakur
*Assistant Examiner* — Elina Sohyun Ahn
(74) *Attorney, Agent, or Firm* — Keating & Bennett, LLP

(57) ABSTRACT

In one aspect, a computer-implemented method includes receiving a signal corresponding to impedance across a patient's chest cavity; filtering the signal using one or more filters that reduce noise and center the signal around a zero baseline; adjusting an amplitude of the filtered signal based on a threshold value; separating the amplitude-adjusted signal into component signals, where each of the component signals represents a frequency-limited band; detecting a fractional phase transition of a component signal of the component signals; selecting a dominant component signal from the component signals based on amplitudes of the component signals at a time corresponding to the detected fractional phase transition; determining a frequency of the dominant component signal at the time corresponding to the detected fractional phase transition; and determining a respiratory rate of the patient based on the determined frequency.

14 Claims, 7 Drawing Sheets

(52) U.S. Cl.
CPC .......... *A61B 5/7203* (2013.01); *A61B 5/7225* (2013.01); *A61B 5/7235* (2013.01)

(58) Field of Classification Search
CPC ....... A61B 5/0816; A61B 5/72; A61B 5/0535; A61B 5/721; A61B 5/6823; A61B 5/0803; A61B 5/085; G06K 9/0053; G16H 50/30
See application file for complete search history.

(56) References Cited

U.S. PATENT DOCUMENTS

| | | | |
|---|---|---|---|
| 8,086,304 B2 | 12/2011 | Broclway et al. | |
| 9,530,425 B2 | 12/2016 | Ricci et al. | |
| 2006/0200035 A1* | 9/2006 | Ricci | A61B 5/333 600/513 |
| 2010/0312075 A1* | 12/2010 | McGonigle | A61B 5/0816 600/529 |
| 2015/0272474 A1* | 10/2015 | Gene | A61B 5/0809 600/533 |

* cited by examiner

SYSTEM FOR PROCESSING RESPIRATORY RATE

CROSS-REFERENCE TO RELATED APPLICATIONS

This application claims the benefit of priority to U.S. Provisional Application No. 62/883,339, filed on Aug. 6, 2019. The contents of which is hereby incorporated by reference in its entirety.

BACKGROUND

This disclosure relates to respiratory rate processing.

Respiratory rate is the rate at which breathing occurs. Typically, the respiratory rate is measured when a patient is at rest and is measured in breaths per minute. Respiratory rates may increase with fever, illness, or other medical conditions and is widely used to monitor the physiology of ill patients. It is measured to facilitate identification of changes in physiology along with other vital signs.

SUMMARY

This disclosure describes systems and techniques related to respiratory rate processing. The described systems and techniques can be used to estimate the average respiratory rate from cyclic variations detected in a raw continuous impedance signal received from a sensor. The respiratory rate processing includes pre-conditioning the impedance signal, followed by rate estimation using a wavelet bank and quarter phase (QP)-domain periodicity tracking. Signal pre-conditioning includes pre-filtering to reduce effects of out-of-band artifacts and to generally improve signal to noise ratio (SNR), followed by adaptive clipping of the filtered signal, via dynamic tracking of local amplitude statistics, to suppress signal spikes and transient increases in signal amplitude. Local losses in signal amplitude may occur due to complete signal loss, such as due to lead detachment, or from lack of impedance variations, such as due to held breath or apnea. Breath rate may not be well-defined under these conditions. The tracked amplitude statistic, itself an estimate of the local amplitude of the filtered signal, is thus used as a basis upon which to qualify the breath rate signal amplitude for sufficient level.

This disclosure incorporates by reference the entire contents of U.S. Pat. No. 7,702,502 filed Feb. 23, 2006, titled "Apparatus for Signal Decomposition, Analysis and Reconstruction," U.S. Pat. No. 7,706,992 filed Feb. 23, 2006, titled "System and Method for Signal Decomposition, Analysis and Reconstruction," U.S. Pat. No. 8,086,304 filed Nov. 26, 2008, titled "Physiological Signal Processing to Determine a Cardiac Condition," and U.S. Pat. No. 9,530,425 filed Mar. 17, 2014, titled "Method and Apparatus for Signal Decomposition, Analysis, Reconstruction and Tracking," which include disclosures of signal decomposition and analysis techniques that are applicable to respiratory rate processing.

In general, in one innovative aspect, a system includes a sensor configured to detect impedance across a patient's chest cavity, a display apparatus, one or more data processing apparatus coupled with the sensor and the display apparatus, and a non-transitory computer readable storage medium encoded with a computer program. The program includes instructions that when executed by the one or more data processing apparatus cause the one or more data processing apparatus to perform operations. The operations include receiving a signal corresponding to impedance across a patient's chest cavity; filtering the signal using one or more filters that reduce noise and center the signal around a zero baseline; adjusting an amplitude of the filtered signal based on a threshold value; separating the amplitude-adjusted signal into component signals, where each of the component signals represents a frequency-limited band; detecting a fractional phase transition of a component signal of the component signals; selecting a dominant component signal from the component signals based on amplitudes of the component signals at a time corresponding to the detected fractional phase transition; determining a frequency of the dominant component signal at the time corresponding to the detected fractional phase transition; and determining a respiratory rate of the patient based on the determined frequency. Separating the amplitude-adjusted signal into the component signals can include filtering the signal using a bank of bandpass filters. Detecting the fractional phase transition of a component signal can include detecting positive-going zero crossings, negative-going zero crossings, positive peaks, and negative peaks of the component signal. Adjusting the amplitude of the filtered signal based on the threshold value can include determining the threshold value based on an average amplitude of the filtered signal and clipping the filtered signal based on the threshold value. Selecting the dominant component signal can include generating, at the detected fractional phase transition of the component signal, a data object containing values representing the time, the amplitude, and a phase corresponding to the component signal at the detected fractional phase transition; and selecting, as the dominant component signal, a component signal having a highest amplitude based on amplitude values contained in data objects generated for the component signals corresponding to the time of the detected fractional phase transition. Determining the frequency of the dominant component signal can be based upon determining time and phase differences between fractional phase transitions. Determining the patient's respiratory rate can include determining an average respiratory rate over a time period.

In another aspect, an apparatus includes a non-transitory computer readable storage medium encoded with a computer program. The program includes instructions that when executed by the one or more data processing apparatus cause the one or more data processing apparatus to perform operations. The operations include receiving a signal corresponding to impedance across a patient's chest cavity; filtering the signal using one or more filters that reduce noise and center the signal around a zero baseline; adjusting an amplitude of the filtered signal based on a threshold value; separating the amplitude-adjusted signal into component signals, where each of the component signals represents a frequency-limited band; detecting a fractional phase transition of a component signal of the component signals; selecting a dominant component signal from the component signals based on amplitudes of the component signals at a time corresponding to the detected fractional phase transition; determining a frequency of the dominant component signal at the time corresponding to the detected fractional phase transition; and determining a respiratory rate of the patient based on the determined frequency. Separating the amplitude-adjusted signal into the component signals can include filtering the signal using a bank of bandpass filters. Detecting the fractional phase transition of a component signal can include detecting positive-going zero crossings, negative-going zero crossings, positive peaks, and negative peaks of the component signal. Adjusting the amplitude of the filtered signal based on the threshold value can include determining the threshold value based on an average amplitude of the filtered signal and clipping the filtered signal based on the threshold value. Selecting the dominant component signal can include generating, at the detected fractional phase transition of the component signal, a data object containing values representing the time, the amplitude, and a phase corresponding to the component signal at the detected fractional phase transition; and selecting, as the dominant component signal, a component signal having a highest amplitude based on amplitude values contained in data objects generated for the component signals corresponding to the time of the detected fractional phase transition. Determining the frequency of the dominant component signal can be based upon determining time and phase differences between fractional phase transitions. Determining the patient's respiratory rate can include determining an average respiratory rate over a time period.

In another aspect, a method includes receiving a signal corresponding to impedance across a patient's chest cavity; filtering the signal using one or more filters that reduce noise and center the signal around a zero baseline; adjusting an amplitude of the filtered signal based on a threshold value; separating the amplitude-adjusted signal into component signals, where each of the component signals represents a frequency-limited band; detecting a fractional phase transition of a component signal of the component signals; selecting a dominant component signal from the component signals based on amplitudes of the component signals at a time corresponding to the detected fractional phase transition; determining a frequency of the dominant component signal at the time corresponding to the detected fractional phase transition; and determining a respiratory rate of the patient based on the determined frequency. Separating the amplitude-adjusted signal into the component signals can include filtering the signal using a bank of bandpass filters. Detecting the fractional phase transition of a component signal can include detecting positive-going zero crossings, negative-going zero crossings, positive peaks, and negative peaks of the component signal. Adjusting the amplitude of the filtered signal based on the threshold value can include determining the threshold value based on an average amplitude of the filtered signal and clipping the filtered signal based on the threshold value. Selecting the dominant component signal can include generating, at the detected fractional phase transition of the component signal, a data object containing values representing the time, the amplitude, and a phase corresponding to the component signal at the detected fractional phase transition; and selecting, as the dominant component signal, a component signal having a highest amplitude based on amplitude values contained in data objects generated for the component signals corresponding to the time of the detected fractional phase transition. Determining the frequency of the dominant component signal can be based upon determining time and phase differences between fractional phase transitions. Determining the patient's respiratory rate can include determining an average respiratory rate over a time period Various other functions and benefits of such systems and methods will be apparent from the foregoing detailed description and claims.

DESCRIPTION OF DRAWINGS

Like reference numbers and designations in the various drawings indicate like elements.

DETAILED DESCRIPTION

Figure 1:
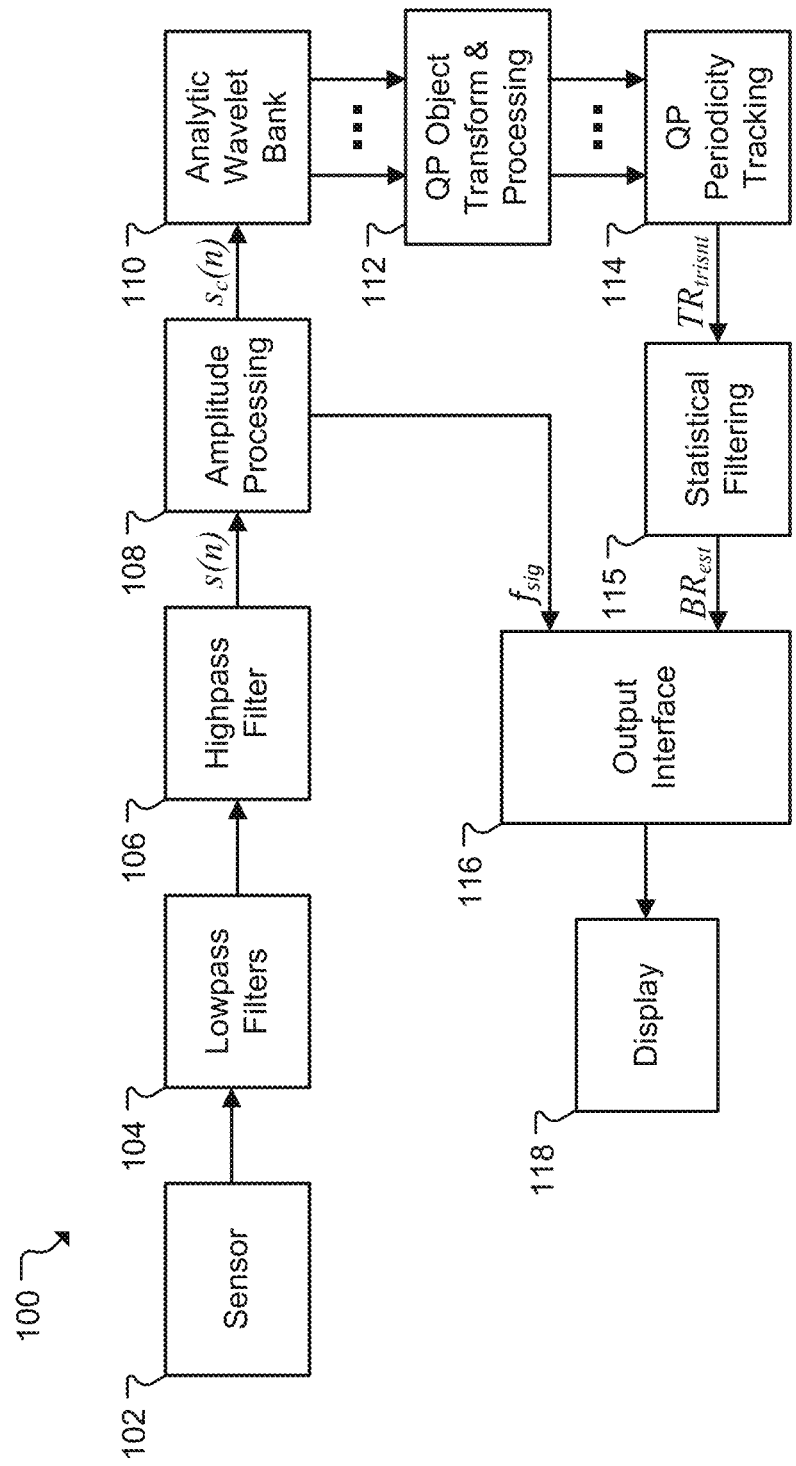
FIG. 1 is a block diagram showing an example of a respiratory rate processing system.

FIG. 1 is a block diagram showing an example of a respiratory rate processing system 100. The system 100 includes electronic components, e.g., hardware and/or software that facilitate respiratory rate processing. In some implementations, portions of the system 100 are included in a patient monitoring device that can continuously collect physiological vital signs data, such as ECG waveforms, heart rate, respiratory rate, oxygen saturation, blood pressure, temperature, and pulse rate. Examples of patient monitoring devices include chest sensors, such as those described in U.S. Publication No. 2015/0302539, filed Oct. 22, 2015, titled "Patient Care and Health Information Management Systems and Methods" and U.S. Publication No. 2016/0228060, filed Feb. 9, 2016, titled "Patient Worn Sensor Assembly," and other sensor assemblies that connect with peripheral devices, such as the sensor assembly described in U.S. Publication No. 2018/0213859, filed Jan. 25, 2018, titled "Sensor Connection Assembly for Integration with Garment," the disclosures of which are hereby incorporated by reference in their entirety. In some implementations, portions of the system 100 are included in a monitoring station that analyzes and displays physiological vital signs data using signals received from one or more peripheral devices, such as a chest sensor, a fingertip probe, an earlobe probe, or a non-invasive blood pressure (NIBP) cuff. Examples of monitoring stations include a bedside monitor and a central server station which are also described in U.S. Publication No. 2015/0302539.

The 100 includes a sensor 102 that injects a high frequency, low amplitude current across the chest cavity, measures the voltage resulting from the current injection, and derives the impedance (magnitude of resistance and phase offset) from the injected current and measured voltage. Current flows less easily through the chest as the lungs fill, so the resistance rises with increasing lung volume. The sensor 102 can be, for example, affixed to the patient's chest.

The raw impedance signal from the sensor 102 may contain high-frequency noise and low-frequency artifacts, which while relatively large, exist mostly outside the expected frequency band that is associated with breath rates (for example, nominally from 5 to 60 breaths per minute (BrPM), or from 0.0833 Hz to 1 Hz, according to physiologic limits and convention). The artifacts can therefore be rejected by applying lowpass filters 104 and a highpass filter 106 to the impedance signal.

The raw impedance signal may contain high-frequency artifacts including spurious noise components generally above 1.5 Hz, along with 50 Hz and 60 Hz power-line EMI products. For embodiments having an impedance signal sample rate $F_{s\_imp}$ of for example 33.33 ... Hz, those EMI products appear at 16.66 ... Hz and 6.66 ... Hz due to aliasing-related frequency-foldover effects. These artifacts may be mitigated by applying a cascade of lowpass filters 104, with various stages designed to match the signal passband and to specifically reject the EMI products. The lowpass filters 104 can be implemented using computationally-efficient scaled-integral kernels. The scaled-integral kernel described in U.S. Pat. No. 7,706,992 can accomplish a lowpass operation efficiently by performing a moving-average lowpass through the transfer function:

$$H_i(z) = \left[ \frac{1-z^{-w_p}}{w_p(1-z^{-1})} \right]^{N_i}$$

having scale parameter $w_p$ and order parameter $N_i$. Specific design criteria are met through setting of the scale and order of the filter kernels.

Signal bandwidth can be matched by placing a lowpass with −6 dB corner frequency set to the highest frequency of interest, for example in this case 1.0 Hz. The scale parameter may be set according to the formula w=round ($F_{s\_imp}*k_{6dBNul}/F_{6dB}$), where $k_{6dBNul}$ is determined numerically to establish the ratio of the corner frequency to the first null frequency of the kernel, and depends upon the order $N_i$ of the kernel. For example, an order of $N_i$=2 may be determined to provide acceptable transition sharpness and out-of-band rejection, particularly in combination with the EMI rejection stages, so that $k_{6dBNul}$=0.44295.

The EMI artifacts can be mitigated by applying two filter kernels in cascade, each having its first response null $F_{null}$ placed respectively at one of the two EMI frequencies, accomplished by setting the scale parameter according to the formula w=round ($F_{s\_imp}/F_{null}$). First-order kernels may be used for the EMI rejection as the response nulls provide complete attenuation at those null frequencies.

Based upon the above derivations, and for the impedance signal sampling period $T_s$=30 milliseconds, examples of parameters for each lowpass filter stage are as follows:

TABLE 1

| Stage | $w_p$ | $N_i$ |
|---|---|---|
| Signal | 15 | 2 |
| EMI 1 | 2 | 1 |
| EMI 2 | 5 | 1 |

The highpass filter 106 is applied to the lowpass filtered impedance signal. The highpass filter 106 removes the large offset near DC introduced by the raw impedance value, so that the signal is centered around a zero baseline, and also rejects as much low-frequency artifact as is practical below the lower nominal respiratory rate band edge (5 BrPM or 0.0833 Hz corresponding to the breath interval of 12 seconds). Given the size of the time scale, a minimum-phase response may be chosen for the highpass filter 106 to minimize time lags in the system due to the filter's intrinsic group delay. Using a recursive-form IIR filter topology may lead to a memory-efficient filter architecture. A second-order response may be chosen as it provides good stability and sufficient rejection in the stop band. The highpass filter 106 is specified according to the following analog-domain transfer function:

$$H_{HP}(s) = \frac{s^2}{s^2 + \frac{\omega_c}{Q}s + \omega_c^2}$$

where $\omega_c$ controls the corner frequency (in radians/sec) and Q controls the resonance of the filter at the corner. A value of Q=0.720 may be chosen to maximize response flatness in the passband and response sharpness at the corner, while substantially minimizing ringing in the impulse response. For this value of Q, the formula $\omega_c=2\pi k_Q f_c$ sets the −6 dB point of the filter at frequency $f_c$ with factor $k_Q$=1.325.

The model may be implemented digitally using a second-order difference equation of the form:

$$a_0 y_{HP}(n)=b_0 x(n)+b_1 x(n-1)+b_2 x(n-2)-a_1 y_{HP}(n-1)-a_2 y_{HP}(n-2)$$

where x(n) and $y_{HP}(n)$ are the signal input and output of the highpass filter 106 at sample time n, respectively. The filter response is determined by the coefficients $a_i$ and $b_j$. To produce a digital filter that approximates the analog model, the bilinear transform may be employed, as it may provide very close matching of analog filter responses, particularly in their passband and transition bands. Examples of resulting digital filter coefficients are as follows:

TABLE 2

| | |
|---|---|
| $a_0$ | 1.0 |
| $a_1$ | −1.97108032037207 |
| $a_2$ | 0.971507303518756 |
| $b_0$ | 0.985646905972705 |
| $b_1$ | −1.9712938119454 |
| $b_2$ | 0.985646905972706 |

The output of the highpass filter 106 is a filtered impedance signal s(n) that is used to estimate the respiratory rate. The filtered impedance signal s(n) may itself be displayed on a display 118, to provide a clean, zero-centered waveform showing the impedance undulations (waves) in response to breaths.

The filtered impedance signal s(n), while improved by the filtering process, may still contain occasional artifacts due to step changes observed in the raw impedance reading. These step changes may be reasonably small as a percentage of the average raw impedance value, but can still be as much as an order of magnitude larger than the relatively small impedance variations due to breath, and so can appear after the above described filtering as relatively large spikes on the observed signal. Additionally, the amplitudes of the impedance variations have been observed occasionally to become much larger than average, by a factor of two or three (or more) for a few breath cycles, resulting in an amplitude transient. This can occur in association with deep breaths, e.g., during pauses while talking, or after brief pauses in breathing. In either case, the large transient condition can in some circumstances over-excite the analytic wavelet bank 110 in the breath rate estimation process, which can lead to inaccuracy or complete loss of breath rate processing for a significant time (e.g., tens of seconds or more, depending upon the size of the transient).

These types of transients can be mitigated in practice through some form of amplitude control. In some implementations, this is achieved by controlled clipping of the signal through an amplitude processing unit 108 that 1) estimates and tracks the local average signal amplitude to form an adaptive threshold, and then 2) clips the signal by limiting its absolute excursion in either direction from zero to that threshold value. Because the spike transients are relatively short in time, such clipping works to reduce their energy, thus mitigating their excitation in the analytic wavelet bank 110. The clipping also limits the excess excitation power of the increased-amplitude waves while still preserving their periodicity information, thus enabling the breath rate processing to continue without disruption throughout those amplitude transients.

The signal amplitude estimate forms a clipping threshold that generally follows the steady-state amplitude of the signal, but is relatively slow to respond to sudden large upward changes in amplitude associated with transient conditions. A clipper based upon this threshold clips most of the transient, while recovering relatively quickly back to the steady-state level.

In some implementations, signal amplitude tracking can be accomplished using a nonlinear averaging (NLA) process, which is generally robust and operates efficiently in real-time. First, a raw amplitude signal is formed by taking the absolute value of the filtered impedance signal s(n), sample-by-sample, to which is applied a nonlinear recursive filter to form a local time-average amplitude estimate. The fundamental block operation of the NLA process is characterized, in an input-output sense, by the following nonlinear difference equation:

$$y(n)=(1-a_n)x(n)+a_n y(n-1)$$

where
x(n)=instantaneous/raw signal amplitude estimate, per sample index n;
y(n)=filtered amplitude estimate of the signal; and $$a_n = \begin{cases} a_r & x(n) \geq y(n) \\ a_f & \text{otherwise} \end{cases}.$$

The NLA block updates output y once per sample n of the impedance signal. The current-sample output value y(n) is the sum of the previous-sample output value multiplied by decay coefficient $a_n$, where $0<a_n<1$, and the current-sample input value x(n) multiplied by complementary coefficient $(1-a_n)$. For a given feedback coefficient $a_n$, the NLA block takes the form of a first-order feedback lowpass filter with unity gain at DC. As such, the output y(n) may be generally considered as the local average of the amplitude signal x(n), where the average is taken over recent past values. The value of the feedback coefficient $a_n$ determines the time-length of the averaging and therefore the settling time of the output in response to a step function input, taking longer to settle as $a_n$ approaches unity.

The transient-rejecting action of the NLA block arises from making the value of $a_n$ dependent upon the relationship between the input and output values. When the input amplitude value x(n) is equal to or above the average amplitude y(n), the feedback coefficient $a_n$ takes on the rising value $a_r$; when the input amplitude is below the average amplitude, the feedback coefficient $a_n$ takes on the falling value $a_f$. By making the rising coefficient closer to unity than the falling coefficient, the filter is made to respond more slowly for input amplitudes above the local average, thus reducing tracking sensitivity for large or fast rises in the instantaneous input signal amplitude. Similarly, the falling coefficient is set for a settling time short enough to facilitate detection of signal loss. The behavior of the signal amplitude tracking under steady-state conditions generally follows the average of the settling times corresponding to the two coefficients.

Through the impulse-invariance mapping of s-plane poles to the z-plane, the digital feedback coefficient $a_n$ is related to the analog time constant $\tau_n$ (expressed in units of seconds) for a first-order analog lowpass filter according to $$a_n = e^{-T_s/\tau_n},$$

where $T_s$ is the sampling period of the impedance signal (also in seconds). The filter output can thus be expected to settle in nominally about $5 \cdot \tau_n$ seconds after a step change in signal amplitude. The rising and falling feedback coefficients $a_r$ and $a_f$ are thus respectively assigned to corresponding rising and falling time constants $\tau_r$ and $\tau_f$ in physical units of seconds.

Proper design of the rising and falling time constants optimizes rejection of large upward transients, smooth tracking during steady-state amplitude conditions without excessive rejection of small upward amplitude variations, and quick downward tracking in response to signal loss. Good amplitude-tracking performance may be obtained using a cascade of three (3) stages of NLA blocks, chained together so that the output y of a preceding block is tied to the input x of the successive block. The input x of the first block in the chain is then the raw absolute-value of the filtered impedance signal s(n), and the output y of the last block in the chain is then used to form the tracked amplitude estimate according to aEst(n)=kAclp·y(n), where kAclp is a scale factor to accommodate optimal clipping levels. Examples of optimal values for the design parameters are as follows:

TABLE 3

| | |
|---|---|
| $\tau_r$ | 10 sec |
| $\tau_f$ | 0.3 sec |
| kAclp | 9 |

Note that for this example the values for time constants $\tau_r$ and $\tau_f$ are the same for all three stages of NLA blocks. At initialization, amplitude tracking values are reset to zero and must rise to steady-state levels, which can take excessive time due to the relatively large value of rising time constant $\tau_r$. To speed the initial settling to steady-state, after reset the time constant is held at $\tau_f$ for an initialization period, e.g., 10 seconds.

The filtered impedance signal s(n) is clipped relative to the tracked amplitude estimate according to the following rule (operated per sample n):

$$s_c(n) = \begin{cases} aEst(n) & s(n) > aEst(n) \\ -aEst(n) & s(n) < -aEst(n) \\ s(n) & \text{otherwise} \end{cases}$$

This produces an amplitude-regularized impedance-variation signal $s_c(n)$ that is used to estimate the respiratory rate.

The tracked amplitude estimate may be used to detect losses in signal amplitude that are consistent with conditions under which the breath rate (and hence its estimation) is not well-defined, e.g., lead detachment, held-breath, and apnea. Signal loss may be generally evidenced as a drop in the value of measure aEst(n), with the lowest values limited by background artifacts due to electrical noise or spurious impedance fluctuations. A threshold value for determining this condition can be set midway between the typical levels encountered during quiescent conditions and those during active breath conditions, to maximize the margin of discriminating the conditions. A flag $f_{sig}$ which is asserted for amplitude levels generally above this threshold, and de-asserted for amplitude levels below the threshold, can then be used for qualifying the signal level for breath rate processing.

In cases where the measure value moves through the qualification threshold region slowly and/or with small ripples superimposed, chattering of the qualification flag could result. This can be mitigated by adding hysteresis to the threshold (e.g., by inversely relating the threshold to the qualification state), thus resulting in two threshold values $thr_U$ and $thr_D$ corresponding to the upward-going and downward-going thresholds, respectively. Also, due to the time lag present in the various processing stages, a time delay may be added to the assertion and de-assertion of the flag so that the indication of signal quality aligns in time with the output of the system. Both objectives can be met by implementing the signal-qualification process with a state machine.

Examples of state definitions and state-transition rules are as follows:

Initialization: State=NOT_QUAL//$f_{sig}$=False

TABLE 4

| Current State | Condition | Next State//Action |
| --- | --- | --- |
| NOT_QUAL | aEst > $thr_U$ | WAIT_Q//Reset Wait_Count |
| WAIT_Q | aEst < $thr_D$ | NOT_QUAL |
| WAIT_Q | Wait_Count > $T_Q$ | QUAL//$f_{sig}$ = True |
| QUAL | aEst < $thr_D$ | WAIT_NQ//Reset Wait_Count |
| WAIT_NQ | Wait_Count > $T_{NQ}$ | NOT_QUAL//$f_{sig}$ = False |

Examples of the parameter values for the amplitude qualification are as follows:

TABLE 5

| Thresholds (Ohms ac) | |
| --- | --- |
| $thr_U$ | 3.08 |
| $thr_D$ | 2.27 |
| Delays (seconds) | |
| $T_{NQ}$ | 2 |
| $T_Q$ | 25 |

Threshold values and delay times may be determined empirically based upon experimental data. Delays for each flag state may be chosen to cause de-assertion of the flag before deterioration of signal conditions and re-assertion of the flag after restoration of signal conditions, seeking to ensure favorable signal conditions only when the associated flag is asserted.

The signal qualification flag $f_{sig}$ can be presented to the output interface 116 as a means of suppressing display of spurious or erroneous breath rate output during unfavorable signal conditions. The signal qualification flag $f_{sig}$ can be utilized for detection of apnea. Signal loss due to lead detachment can be distinguished from signal loss due to apnea through detection of contact loss (e.g., through the raw impedance showing an out-of-range value condition). Apnea can thus be detected when signal qualification flag $f_{sig}$ is False while lead contact is intact.

The breath rate estimation process may be based upon a method for tracking and estimation of rates, based upon embedded periodicities, as described in U.S. Pat. No. 9,530,425. The method provides accurate, robust rate estimation at low computational cost. The method leverages the techniques described in U.S. Pat. No. 7,706,992, and extends those techniques to enable tracking fundamental rates of underlying components in the input signal over a wide rate range (e.g., greater than one octave). The breath rate estimation process in the current example covers a nominal physiologic rate range of 5 to 60 BrPM, a range of over 3.5 octaves. For the breath rate estimation, processing and tracking of components may be performed in quarter-phase (QP) space. In this space, updates are performed when the input signal undergoes a change at points of significant information (also referred to as "significant points") without loss of measure or timing accuracy. This "intelligent sampling" can translate to significant computational savings, since QP-based information updates typically occur much less frequently than signal updates, which occur once per sampling period.

The amplitude-regularized impedance-variation signal $s_c(n)$ may be first processed with a multi-band analytic wavelet bank 110 to analyze the signal over a set of rate bands as described in U.S. Pat. No. 9,530,425, covering the range of expected breath rates. The band outputs are analytic component signals, to which are applied a QP transform (as described in U.S. Pat. No. 7,706,992) by the QP object transform and processing unit 112 to detect the extrema and zero-crossings of the component signals. At these points are formed QP objects containing key time-frequency information updates associated with periodicities in the signal. This process results in an array of streams of QP objects, one stream per component signal (or band). The QP objects then may be processed in QP space by the QP periodicity tracking unit 114 to identify and track the dominant periodic component (as described in U.S. Pat. No. 9,530,425) identified in the amplitude-regularized impedance-variation signal $s_c(n)$. From this component may be extracted its local periodic properties with high time precision to determine the local average breath rate.

The analytic wavelet bank 110 is generally designed as a bank of bandpass filters with adjacently-spaced band centers. Each bandpass filter in the bank responds by varying amounts to periodicities present in the bank input signal according to its frequency response, having the greatest output amplitude for frequencies closest to the center frequency of the bandpass. For a signal applied to the filter bank input containing (quasi) periodic components, the filters having the greatest output amplitude at a point in time, relative to their neighbors, will be those frequency bands with centers closest to the frequencies of those signal components. A tracing of the band amplitudes as a function of band frequency at that time point would reveal "peaks" at those associated frequencies. Finding and tracking these amplitude peaks as a function of time, along with the underlying information in the bands indexed by those peaks, forms the underlying principle of the bandpass filter bank. Another advantage of using bandpass filters is that each filter in the bank has relatively narrow bandwidth, thus having generally higher SNR relative to the associated frequency component.

A design consideration for the filter bank is the so-called "time-frequency frame" of the system, controlled through the "Q" (relative bandwidth) of the bandpass filters. Closely tied to the time-frequency frame is the frequency spacing of the bands. Excess band overlap represents a finer sampling of the frequency domain but comes at increased computation expense for what may constitute redundant spectral information. However, insufficient band overlap can lead to an excess of amplitude loss in the crossover region between band centers, leaving "holes" in the spectral representation of the signal, and in extreme cases leading to ambiguity in the spectral peak patterns. Higher Q will create a narrower filter bandwidth, allowing filters to be more closely spaced in frequency for a given amount of band overlap, thus providing increased frequency resolution. However, implementing a narrow filter bandwidth necessarily requires having an impulse response that is wider in time, which in turn translates to lower time resolution, as well as increased processing latency, which can lead to excessive response lag in the system. Hence the choice of Q represents a tradeoff between frequency resolution and time resolution and/or response time.

As described in U.S. Pat. No. 9,530,425, the processing in QP space allows for time-frequency information to be captured with much higher precision in both time and frequency than conveyed by simply using the center frequency of a given band as the rate estimate. This property can relax the requirement for frequency resolution among the band centers strictly to resolve frequency. In theory, only a minimum of two bands per octave would be needed to isolate the fundamental harmonic from the second harmonic of the input periodic component, though in practice more bands are required for low inter-band response crossover loss.

The band centers may be distributed so that their spacing is not excessively sparse over frequency ranges where the breath rate processing should express the greatest precision, such as for normal ranges where long-term trends may be monitored and/or smoothness of system response is desired. For monitoring breath rates, a band spacing of roughly 1-2 BrPM can produce the desired response smoothness over the physiologic rate range up to 30 BrPM. Rates above this, being associated with hyperventilation, require faster response time to a greater degree than response smoothness, so the Q can be set lower in these ranges, thus allowing the resolution requirement to be relaxed in the upper rate range. Using a purely logarithmic band spacing over the entire rate range can result in over-compression of the band spacing at the low end of the frequency range and/or excessively sparse band spacing at the high end, while using a purely linear band spacing can result in the opposite unfavorable conditions. A curve for the target band spacing may follow a power law, according to the formula:

$$f_n = (g_1 + n(g_2 - g_1)/(N_b - 1))^p$$

where $g_1 = \sqrt[p]{f_0}$, $g_2 = \sqrt[p]{f_{N_b}}$, and $n \in \{0, 1, \ldots, N_b - 1\}$ with the target rates of $f_0$=5 BrPM, $f_{N_b}$=60 BrPM, target number of bands $N_b$=24, and power law p=1.5. This distribution results in band spacings with an average of approximately 7.2 bands per octave and a minimum of 3.4 bands per octave.

The analytic wavelet bank 110 can be implemented using the Parallel-Form Kovtun-Ricci Wavelet Transform with analytic component bands as described in U.S. Pat. No. 7,706,992. In addition to the scaled integral and scaled difference kernels, the analytic wavelet bank 110 can include in the kernel cascade an additional kernel type referred to here as a scaled comb kernel, having z-domain transfer function:

$$H_{cp}(z) = \left[\frac{1 - z^{-2k_p c_p}}{c_p(1 - z^{-2k_p})}\right]^{N_{cp}}$$

with scale parameters $k_p$ and $c_p$, and order parameter $N_{cp}$ for band p. The intrinsic delay of this kernel is $D_{cp}=N_{cp} \cdot k_p \cdot (c_p - 1)$. The frequency response of the scaled comb kernel for $N_{cp}$=1 is a Dirichlet function, which closely approximates a sinc function at its first mainlobe around DC and then repeats these mainlobes over frequency at an interval controlled by scale parameter $k_p$ (specifically, at a frequency spacing of $F_s/(2 k_p)$ where $F_s$ is the sampling rate). The value $k_p$ can be set to the same scaling value $k_p$ as appears in the expression for the scaled difference kernel. This will center the first repeated mainlobe of the scaled comb over the first mainlobe of the scaled difference, defining a new, more selective bandpass function centered at the peak of the mainlobe. The scaled comb features response nulls to either side of each repeated mainlobe, spaced away from each center according to scale parameter $c_p$, such that for $c_p$=2 the nulls are halfway between the mainlobe centers, and for larger $c_p$ the nulls move proportionally closer to the mainlobe centers. These nulls have the effect of narrowing the mainlobe bandwidth, effectively increasing the Q of the filter. The Q is also increased with increasing order $N_{cp}$, so that this kernel features two parameters by which Q may be additionally controlled. Performance may be further enhanced in that the increased Q obtained due to the added side nulls, even for $c_p$=2, results in less impulse response widening than when obtaining a similar Q via increasing filter order alone. On the other hand, increasing the order does reduce the height of the sidelobes between the mainlobe images, and so the order $N_{cp}$ becomes the primary means to control stopband rejection in the regions just beyond the first passband nulls.

Observed in a broadband sense, the scaled comb kernel acts as a comb filter, with a lobe around DC and repeating lobes according to scale $k_p$. To obtain a pure bandpass response, it may be desired to isolate the first repeat of the mainlobe response above DC, which is centered at frequency $F_s/(2 k_p)$. To reject the lobe at DC, the scaled difference kernel may be utilized, as it has a primary response null at DC. The scaled integral kernel may be then utilized to reject the mainlobe images above the first, as well as to provide overall smoothing of the impulse response. Using these two kernels in the role of stopband rejection tends to not require high orders in practice (e.g., order 4 may provide sufficient out-of-band rejection).

The parameters for programming the bandpass wavelet responses are therefore $k_p$, $c_p$, $N_{cp}$, $N_{dp}$, $w_p$, $N_{ip}$. For the $p^{th}$ bandpass, $k_p$ controls the center frequency, and Q is controlled by the combination of (primarily) $c_p$, and (secondarily) $N_{cp}$ and scaled-derivative order $N_{dp}$. The parameters $N_{cp}$ and $N_{dp}$ control the stopband rejection near DC, and the scaled-integral scale $w_p$ and order $N_{ip}$ control the stopband rejection above the passband.

This family of bandpass wavelets can be computationally efficient and features linear phase response per band. As described in U.S. Pat. No. 7,706,992, the bank of wavelets performs a time-frequency transform. This transform may be implemented with extra time delays per band to maintain time alignment across the bands. While preserving timing information between the bands in the transform is useful for extracting properties within multiple components in the underlying signal, to achieve this requires accommodating the longest latency in the bank, e.g., that of the lowest-rate band, while adding increasing latency to the higher-rate bands. The lowest supported breath rate may be 5 BrPM, carrying with it a fundamental period of 12 seconds per breath. As the band wavelets typically support on the order of several cycles in their impulse response, this imposes a large lag for the higher bands. An objective is to estimate the frequency of only the (single) fundamental component of the breath rate, and with as small a latency as possible to provide fast response to rapidly increasing breath rates, such as during sudden onsets of hyperventilation. Therefore, the analytic wavelet bank 110 can be implemented without time alignment between bands, and so no added delay elements, such that each band exhibits only the intrinsic delay of its own wavelet structure. A property of the bank 110 resulting from this is that intrinsic delay will generally decrease with increasing band center frequency and/or rate.

The Q of the filter bank can then be set according to the desired inter-band overlap point, i.e., the drop in amplitude, relative to the amplitude response peak, to the point where a given band's amplitude response crosses that of the next neighboring band. For resolving a single primary frequency component, an overlap at the −6 dB point is theoretically sufficient to ensure coverage of amplitude over the entire range of the bank, to guard against amplitude ambiguity that would occur due to a "hole" in coverage between bands. In some implementations, an extra margin of overlap is implemented for analysis banks, to provide a certain amount of smoothing in the transition between bands. The overlap point can be placed at nominally −1 dB (minimum −1.3 dB) to ensure smooth coverage while still maintaining a high amount of selectivity.

Per the above descriptions and derivations, and for the sampling period as specified previously for the impedance signal, the bandpass wavelets of the analytic wavelet bank 110 can be implemented using the following design parameters:

TABLE 6

| Band | $F_{Cp}$ nominal (BrPM) | $k_p$ | $c_p$ | $N_{cp}$ | $N_{dp}$ | $w_p$ | $N_{ip}$ |
|---|---|---|---|---|---|---|---|
| 1 | 5.20 | 182 | 2 | 2 | 4 | 121 | 4 |
| 2 | 6.39 | 148 | 2 | 2 | 4 | 99 | 4 |
| 3 | 7.63 | 124 | 2 | 2 | 4 | 83 | 4 |
| 4 | 8.93 | 106 | 2 | 2 | 4 | 71 | 4 |
| 5 | 10.30 | 92 | 2 | 2 | 4 | 61 | 4 |
| 6 | 11.82 | 80 | 2 | 2 | 4 | 54 | 4 |
| 7 | 13.15 | 72 | 2 | 2 | 4 | 48 | 4 |
| 8 | 14.78 | 64 | 2 | 2 | 4 | 43 | 4 |
| 9 | 16.47 | 58 | 2 | 2 | 6 | 39 | 4 |
| 10 | 18.37 | 52 | 2 | 2 | 6 | 35 | 4 |
| 11 | 19.91 | 48 | 2 | 2 | 6 | 32 | 4 |
| 12 | 21.75 | 44 | 2 | 2 | 6 | 29 | 4 |
| 13 | 23.87 | 40 | 2 | 2 | 6 | 27 | 4 |
| 14 | 25.18 | 38 | 2 | 2 | 6 | 25 | 4 |
| 15 | 28.08 | 34 | 2 | 2 | 6 | 23 | 4 |
| 16 | 29.78 | 32 | 2 | 2 | 6 | 22 | 4 |
| 17 | 32.52 | 30 | 3 | 2 | 6 | 20 | 4 |
| 18 | 34.81 | 28 | 3 | 2 | 6 | 19 | 4 |
| 19 | 37.44 | 26 | 3 | 2 | 6 | 18 | 4 |
| 20 | 40.65 | 24 | 3 | 2 | 6 | 16 | 4 |
| 21 | 44.29 | 22 | 3 | 2 | 6 | 15 | 4 |
| 22 | 48.65 | 20 | 3 | 2 | 6 | 14 | 4 |
| 23 | 54.20 | 18 | 3 | 2 | 6 | 12 | 4 |
| 24 | 60.88 | 16 | 3 | 2 | 6 | 11 | 4 |

The values $F_{Cp}$ are the center frequencies of the bands, defined as the frequency where the $p^{th}$ band exhibits its peak amplitude response. Full coverage of the desired rate range may be achieved with 24 bands. For purely logarithmically-spaced bands, the band crossover points are regularized if the Q parameters of the bands are held constant (resulting in a so-called "constant-Q" bank). Since the band spacing in this bank is not logarithmic but rather supra-linear, maintaining regularity in the band-crossover points may require increasing certain Q parameters at well-placed points along the frequency axis (determined empirically for best band crossover characteristics). Thus, several representative responses for various scales exist, one for each specific Q in the bank.

Figure 2A:
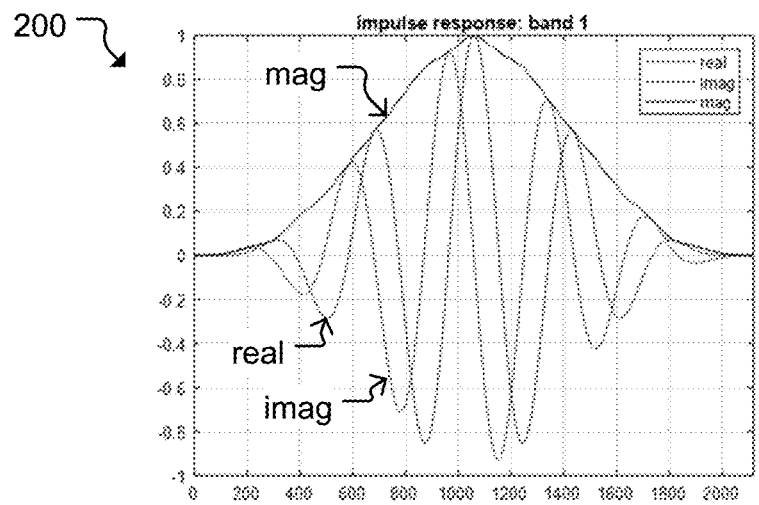
FIGS. 2A-C are plots showing impulse responses for bands of the analytic wavelet bank of the respiratory rate processing system.
Figure 2B:
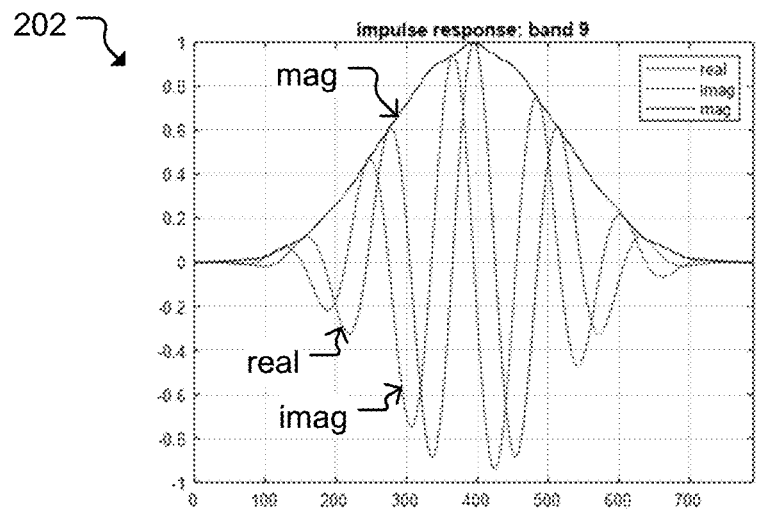
Figure 2C:
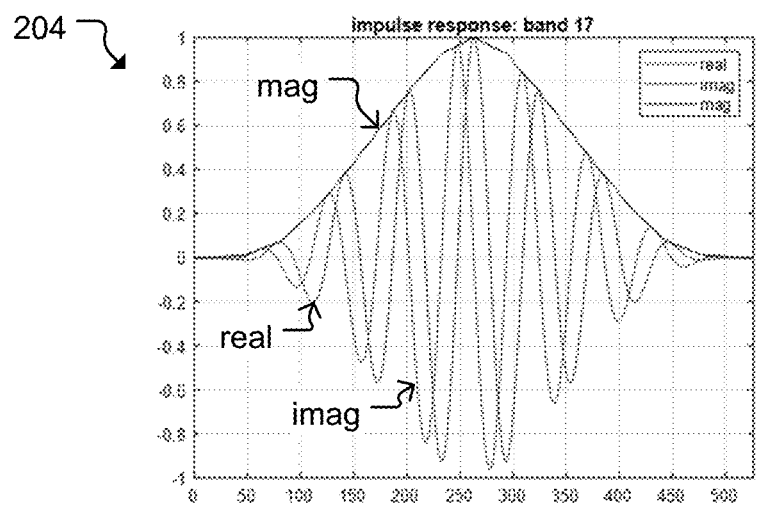
Figure 2D:
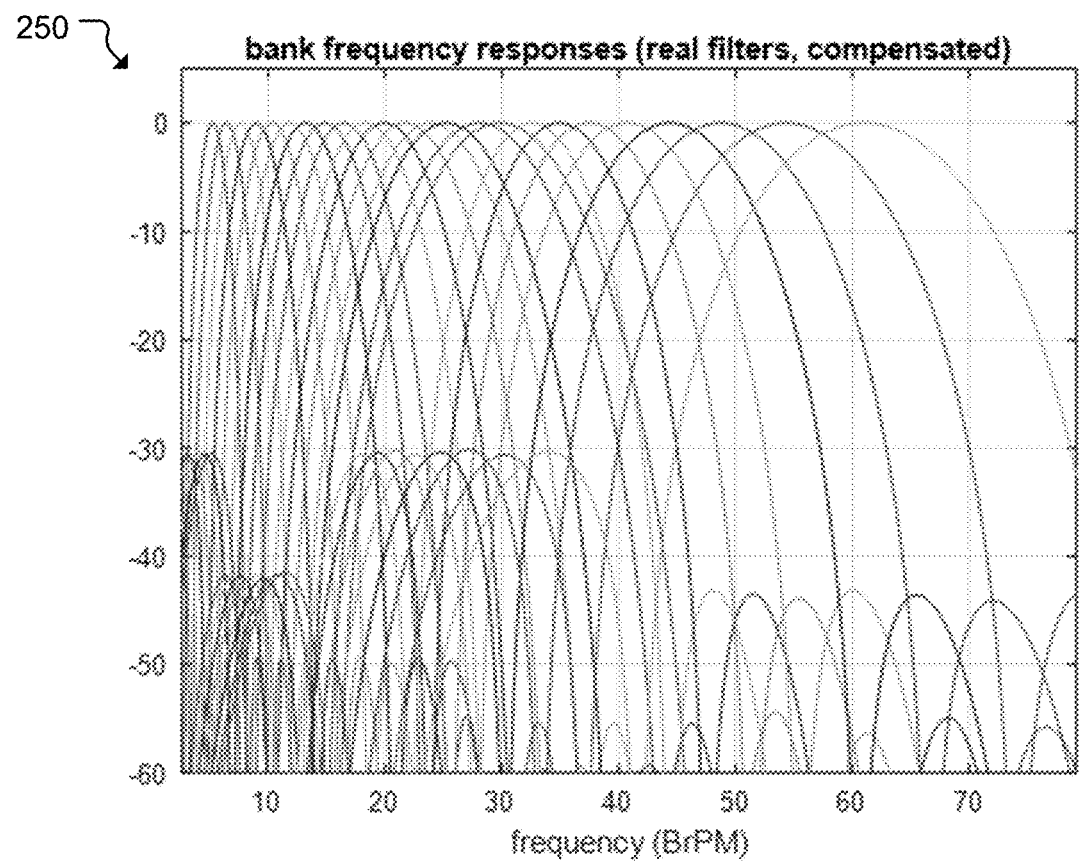
FIG. 2D is a plot showing frequency responses for the real part of the analytic wavelet bank.

FIGS. 2A-C are example plots 200, 202, 204 showing the impulse responses for bands 1, 9, and 17, respectively (specifically, each of the lowest-frequency analytic wavelet bands for each range of bands having specific Q in the bank). The time-domain impulse responses resulting for these wavelets feature an effective time length of between 3 to 5 cycles, and so represent very good time resolution for locally-cyclic behavior. For each of these plots, the maximum-time-amplitude point is normalized to unity, and the x-axis is time in units of samples. Since the wavelets are analytic, the impulse responses are complex-valued. The "real" and "imag" traces are the real and imaginary parts of the impulse response, respectively. The "mag" trace is the instantaneous complex magnitude at each time point. FIG. 2D is an example plot 250 showing frequency responses for the real part of the analytic wavelet bank after the compensation described below.

To ensure calibration of the relative responses across the filter bank, the band output signals may be normalized to unity gain at the band centers. Calibration factors $A_{NR}$ and $A_{NI}$ are determined by evaluating the real-part and imaginary-part amplitude responses (respectively) at their center frequencies $F_{Cp}$ and taking the multiplicative inverse. In some implementations, the real and imaginary filter outputs are multiplied by their respective calibration factors, resulting in a calibrated filter bank. Accordingly, the calibration factors for each corresponding band are as follows:

TABLE 7

| Band | $A_{NR}$ | $A_{NI}$ |
|---|---|---|
| 1 | 2.0470927 | 2.0542274 |
| 2 | 2.0648825 | 2.0722489 |
| 3 | 2.0667424 | 2.0741332 |
| 4 | 2.0686815 | 2.0760980 |
| 5 | 2.0390806 | 2.0461123 |
| 6 | 2.0915792 | 2.0992999 |
| 7 | 2.0545645 | 2.0617964 |
| 8 | 2.0773432 | 2.0848744 |
| 9 | 2.0907693 | 2.0959883 |
| 10 | 2.0935583 | 2.0988033 |
| 11 | 2.0644915 | 2.0694699 |
| 12 | 2.0309706 | 2.0356498 |
| 13 | 2.1015432 | 2.1068628 |
| 14 | 2.0252624 | 2.0298917 |
| 15 | 2.1075442 | 2.1129203 |
| 16 | 2.1590316 | 2.1649017 |
| 17 | 2.0963027 | 2.0978594 |
| 18 | 2.1534026 | 2.1551208 |
| 19 | 2.2225780 | 2.2245021 |
| 20 | 2.0942442 | 2.0957954 |
| 21 | 2.1668987 | 2.1686566 |
| 22 | 2.2597466 | 2.2617862 |
| 23 | 2.0898030 | 2.0913422 |
| 24 | 2.1893575 | 2.1911826 |

Figure 3:
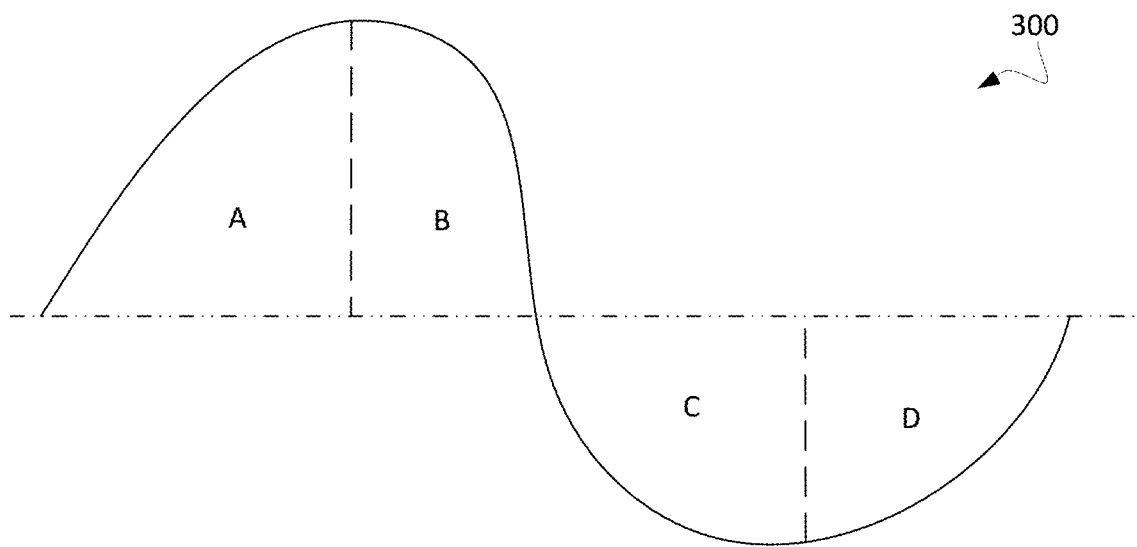
FIG. 3 is a waveform illustrating a cycle from one component signal that is broken up into four quarter-phases.

Referring to FIG. 1, the QP object transform and processing unit 112 detects QP transitions on each of the component signals received from analytic wavelet bank 110. FIG. 3 is a waveform 300 illustrating an example where a cycle from one component signal is broken up into four quarter-phases, labeled as A, B, C, and D. This component signal is broken up into and, in some implementations, defined according to certain unique features such as the positive-going and negative-going zero crossings, and the positive and negative peaks of the component signal. These unique features are shown in a table format below:

TABLE 8

| QP Label | Starts at | Ends at |
| --- | --- | --- |
| A | Positive-going zero crossing | Positive peak |
| B | Positive peak | Negative-going zero crossing |
| C | Negative-going zero crossing | Negative peak |
| D | Negative peak | Positive-going zero crossing |

Referring again to FIG. 1, the QP object transform and processing unit 112 forms, at each QP transition, a QP object (e.g., a data structure) which collects QP attributes (e.g., in data fields) as described in U.S. Pat. No. 7,706,992. For purposes of breath rate estimation, the QP objects contain the phase value (signified by a phase label $L_{QP}$), the time value $t_{QP}$ and the component amplitude $a_{QP}$ at the time point of QP detection, along with the index of the band for the underlying component. Collecting the current QPs at the current time point into an array across the bands forms a QP state vector, indexed by band, and updated upon any QP object update on any band, thus comprising a QP State Update (in accordance with U.S. Pat. No. 7,706,992). The concentrated time-frequency information contained in this state vector forms the basis to enable the identification and tracking of dominant frequency components, and the high-precision estimation of their instantaneous frequencies and amplitudes.

The breath rate estimate is based upon computing the atomic period of the rate component at each QP State update, specifically on all QP Objects (bands) that are updating upon a QP State update. As described in U.S. Pat. No. 7,706,992, this estimate is based upon computing time and phase differences from one QP Object update to the next (i.e., a QP Object Transition), which in turn yields information about the period of the underlying frequency component with high precision. The atomic period estimation for a given QP Object update may be expressed as follows:

$$TR_{QP} = dT_{QP}/(60 \cdot dP_{QP})$$

The value $TR_{QP}$ corresponds to the atomic breath period in units of minutes-per-cycle, (minutes per breath). The value $dT_{QP}$ corresponds to the time interval from the previous QP Object update to the current one, in units of seconds. The value $dP_{QP}$ corresponds to the advance in phase value associated with the number of quarter-phase labels that were traversed from the previous QP Object update to the current one, and is evaluated according to the following table:

TABLE 9

| Number of QP phase labels traversed | Description of QP State Transition | Phase change $dP_{QP}$ (in units of cycles) |
| --- | --- | --- |
| 0 | No change | 0 |
| 1 | Basic phase advance | 0.25 |
| 2 | Phase advance with skip | 0.5 |
| −1 | Phase reversal | −0.25 |

The number of QP phase labels traversed corresponds to the increment encountered along the cyclic sequence . . . A→B→C→D→A . . . in the current QP Object transition, according to U.S. Pat. No. 7,706,992. The basic phase advance (e.g., a label increment of one) is by far the most common phase change. A phase change of zero is unlikely, but possible during noise or transients, particularly at startup. A phase label change of −1 or 2 is similarly possible in the case of a sudden phase reversal, typically associated either with transients in the signal, or more commonly, with QP Object updates occurring on bands located far from any significant periodic components in the signal and thus exhibiting low relative band amplitude and/or SNR. The atomic breath period estimation $TR_{QP}$ may be then updated at each QP Object update of a band where the QP phase label has changed and $dP_{QP}$ is greater than zero.

For forming stable QP statistics, the QP amplitudes and atomic periods each smoothed through scaled integral kernels operating in QP space. The integral scales may be set to 4 QP's, to naturally match one cycle of the underlying wavelet scale. First-order scaled integral kernels may provide sufficient smoothing at this stage. The smoothing operation results in estimates of the instantaneous component amplitude $a_{inst}$ and instantaneous breath period $TR_{inst}$ evaluated on each band at its associated QP Object update. These estimates are then appended onto the QP State vector, per band, forming an instantaneous amplitude vector and instantaneous breath period vector that are both also updated at each QP State Update.

At each QP State Update, the current state of the associated smoothed instantaneous amplitudes, taken across the bands, forms a QP amplitude spectrum. Locally-periodic components arising from the undulation of the breath rate input signal will tend to excite those bands having center frequencies (central periods) in the neighborhood of the underlying component's period. The QP amplitude spectrum at a given QP time point will therefore generally exhibit peaks at those corresponding band indices, with the dominant component exhibiting a dominant (or highest-amplitude) peak. Observation of the Fourier-series properties of the breath signal waveforms (specifically, the amplitudes of the harmonics in the series) shows that in practice, the first harmonic in the series tends to always have the highest amplitude, and so will appear as the dominant periodic component. This property tend to hold true even if the breath signal waveform is undergoing the aforementioned clipping process. Since the period of the first harmonic also corresponds to the cyclic period of the signal waveform, the band having the highest amplitude in the QP amplitude spectrum is therefore associated with the fundamental rate component of the underlying cyclic signal waveform.

The QP periodicity tracking unit 114 therefore performs the following steps at each QP State Update:
  selecting of the dominant band by finding the maximum amplitude across the QP amplitude spectrum.
  If the maximum-amplitude band also experienced a QP Object update, then:
    flagging a tracking update,
    updating the tracked band index with the index of the dominant band,
    updating the instantaneous tracked amplitude $a_{trInst}$ with the instantaneous amplitude $a_{inst}$ of the dominant band, and
    updating the instantaneous tracked breath period $TR_{trInst}$ with the instantaneous breath period $TR_{trInst}$.
The instantaneous tracked breath period estimate value $TR_{trInst}$ thus represents the instantaneous period of breath signal undulations, in minutes per cycle, updated four times per local cycle according to the quarter-phase processing.

A statistically-based smoothing filter 115 can be applied to the instantaneous tracked breath period estimate value $TR_{trInst}$ to produce a smoothed moving estimate $TR_{est}$ of the breath interval. The smoothing filter 115 is designed to remove any remaining large, outlying transient excursions from the final output and to generally stabilize the output readings. A smoothing time $T_{sm}=10$ seconds may produce an acceptable level of smoothing while keeping time lag as low as possible. In some implementations, the processing latency up to the smoothing filter 115 adds up to approximately 4 cycles (~3 cycles in the analytic wavelet bank 110 plus 1 cycle in the QP MA process), or approximately 20 seconds for a nominal breath rate of 12 BrPM (breath period of 5 seconds). This results in a nominal system latency of 30 seconds, which is in line with clinical practice.

The averaging within the smoothing filter 115 can be updated at each tracking update using the values of $TR_{trInst}$ occurring within the interval $T_{sm}$ seconds preceding (and including) the current tracking update, resulting in the final breath period estimate $TR_{est}$ expressed in minutes-per-cycle. Finally, the breath rate estimate may be evaluated as $BR_{est}=1/TR_{est}$ and expressed in BrPM.

The smoothing filter 115, rather than performing a simple moving average, may compute a smoothed median by taking the averages of the central values, in a percentile sense, over a range around the pure median. The central-range average may be set to include those values in the quartile range both above and below the median value, chosen to preserve robustness against outliers while also producing well-smoothed outputs over time.

The respiratory rate processing system 100 can be useful in any setting where a patient's breath rate is to be monitored or statistically analyzed, including intensive care, operating, recovery, and emergency and hospital ward settings. The system 100 can provide continuous and immediate breath rate values, which are of critical importance in emergency medicine and are also very useful for patients with respiratory or cardiac problems.

Figure 4:
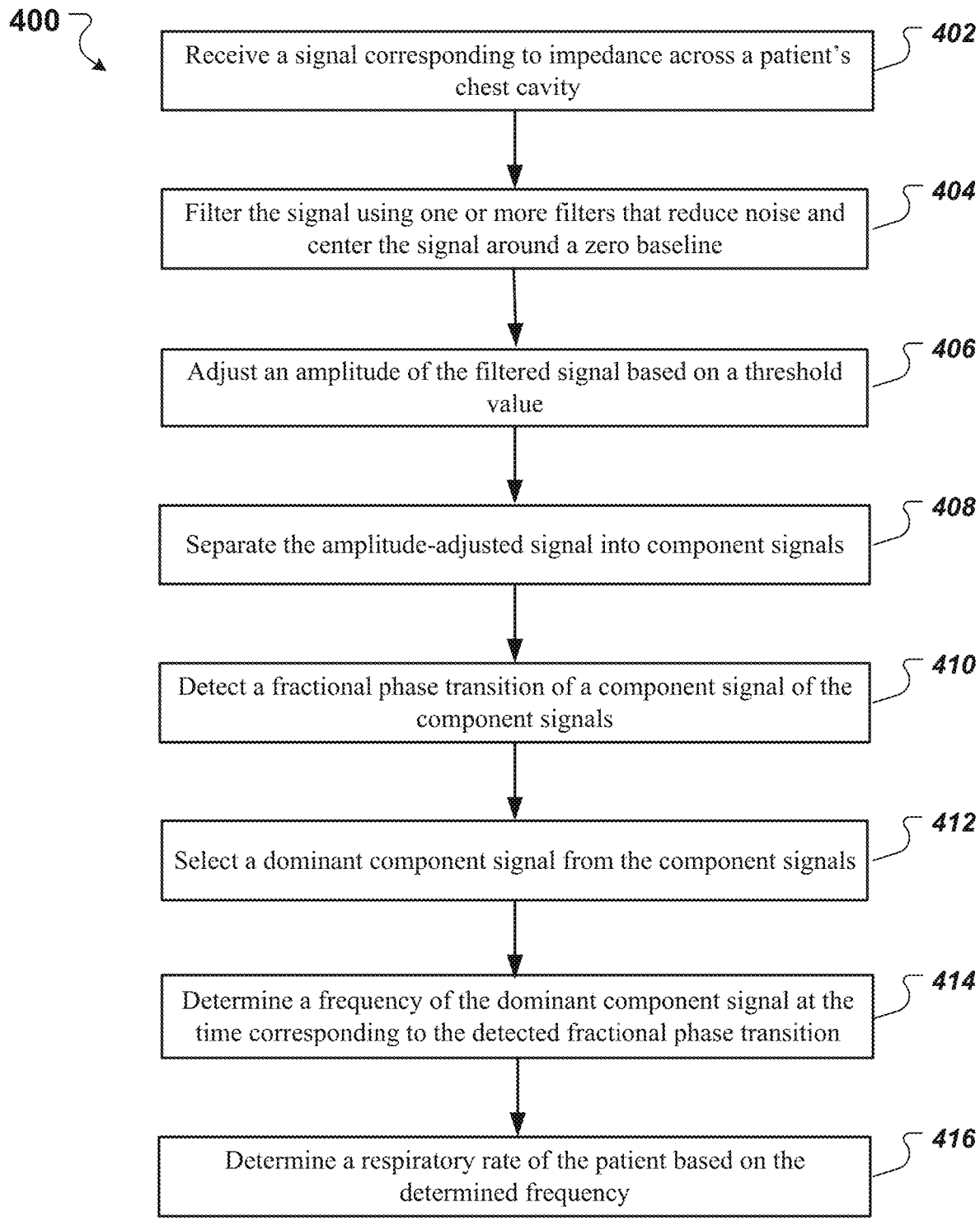
FIG. 4 is a flowchart showing examples of operations performed by a respiratory rate processing system.

FIG. 4 is a flowchart showing examples of operations 400 performed by a respiratory rate processing system. The operations 400 may be performed by a system of one or more computers, such as the system of FIG. 1. The operations 400 may include details that have been discussed above.

At 402, a signal corresponding to impedance across a patient's chest cavity is received. At 404, the received signal is filtered using one or more filters that reduce noise and center the signal around a zero baseline.

At 406, an amplitude of the filtered signal is adjusted based on a threshold value. Adjusting the amplitude of the filtered signal based on the threshold value can include determining the threshold value based on an average amplitude of the filtered signal and clipping the filtered signal based on the threshold value.

At 408, the amplitude-adjusted signal is separated into component signals, where each of the component signals represents a frequency-limited band. Separating the amplitude-adjusted signal into the component signals can include filtering the signal using a bank of bandpass filters.

At 410, a fractional phase transition of a component signal of the component signals is detected. Detecting the fractional phase transition of a component signal can include detecting positive-going zero crossings, negative-going zero crossings, positive peaks, and negative peaks of the component signal.

At 412, a dominant component signal is selected from the component signals based on amplitudes of the component signals at a time corresponding to the detected fractional phase transition. Selecting the dominant component signal can include (i) generating, at the detected fractional phase transition of the component signal, a data object containing values representing the time, the amplitude, and a phase corresponding to the component signal at the detected fractional phase transition; and (ii) selecting, as the dominant component signal, a component signal having a highest amplitude based on amplitude values contained in data objects generated for the component signals corresponding to the time of the detected fractional phase transition At 414, a frequency of the dominant component signal at the time corresponding to the detected fractional phase transition is determined. Determining the frequency of the dominant component signal can be based upon determining time and phase differences between fractional phase transitions.

At 416, a respiratory rate of the patient is determined based on the determined frequency. Determining the patient's respiratory rate can include determining an average respiratory rate over a time period.

Figure 5:
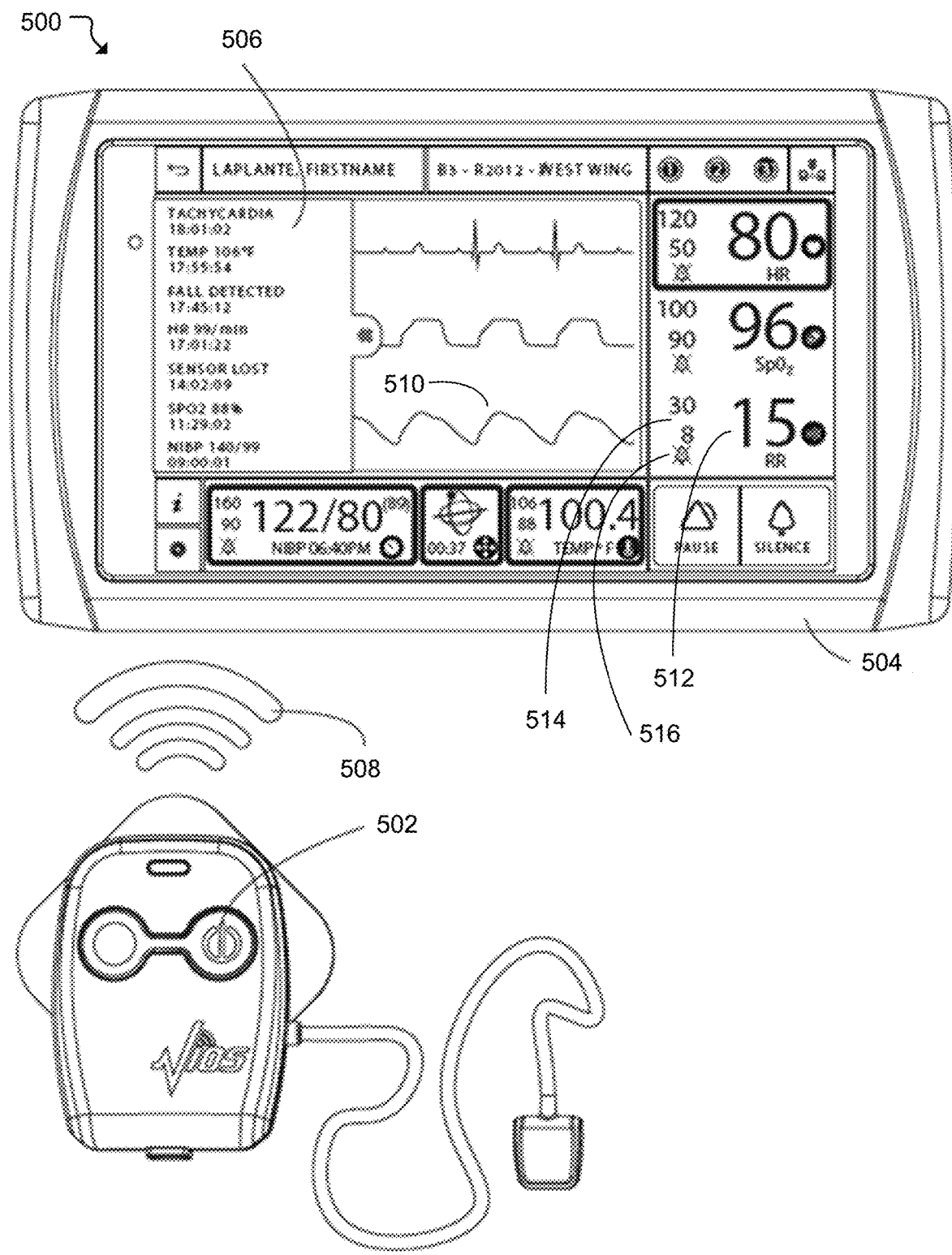
FIG. 5 shows an example of a respiratory rate processing system that includes a patient worn sensor in communication with a display device.

FIG. 5 shows a system 500 that includes a patient worn sensor 502 in communication with a display device 504, such as a display of a bedside monitor, a central server station, or a mobile device as described in U.S. Publication No. 2015/0302539. The display device 504 displays information for a patient. The display device 504 can display a user interface 506 that includes information received from the patient worn sensor 502 and/or information associated with a patient associated with the patient worn sensor 502. The patient worn sensor 502 can be, for example, a chest sensor as described in U.S. Publication No. 2015/0302539. The patient worn sensor 502 can include contacts for attaching to the skin of a patient and recording various patient vital signs such as blood pressure, body temperature, respiratory rate, body impedance, blood oxygenation, heart rhythm (via ECG), and heart rate.

The patient worn sensor 502 can wirelessly communicate with the display device 504 through a wireless connection 508 using a wireless communication protocol such as, for example, Bluetooth, WiFi, or a cellular protocol. The patient worn sensor 502 can transmit vital sign information for the patient to the display device 504 through the wireless connection 508. In some implementations, the patient worn sensor 502 can perform processing on the collected vital sign information, such as the respiratory rate processing described above, prior to transmission of the information to the display device 504, while in some implementations, the patient worn sensor 502 can transmit raw vital sign information to the display device 504 instead of or in addition to processed information.

The display device 504 can be a touch screen device, such as a tablet, that is capable of receiving touch screen inputs. In some implementations, the display device 504 can receive input from a keyboard, mouse, input buttons, or one or more devices capable of recognizing voice commands. In some implementations, the display device 504 can be controlled using a device in wireless communication with the display device 504, such as a mobile phone. In some implementations, the display device 504 is a "headless" device that does not include direct user input and/or output functionality, but rather merely serves as a processing device for processing raw vital sign information received from the patient worn sensor 502, detecting alarm states, transmitting alerts to other devices in communication with the display device 504, and transmitting patient information to one or more central servers. In such cases, the display device 504 would not include a display.

The user interface 506 displays information for a patient associated with the patient worn sensor 502. For example, electrodes of the patient worn sensor 502 can be in contact with the patient's skin and collect vital sign information which is transferred to the display device 504 through the wireless connection 508, processed by the display device 504, and displayed as part of the user interface 506. The user interface 506 shows various vital sign waves and numeric levels.

For example, the user interface 506 shows a respiratory waveform 510 for the patient as well as a numeric respiratory rate (RR) value 512 for the patient. The respiratory waveform 510 and respiratory rate value can be determined, for example, according to the processes described above with respect to FIGS. 1-4. In the example shown, the respiratory rate value 512 for the patient is 15 breaths per minute. The user interface 506 indicates an acceptable respiratory rate range 514 for the patient as falling between 8 and 30 breaths per minute. Being as the current breath rate 512 for the patient of 15 breaths per minute falls within the indicated acceptable range 514, there is not currently an alarm state for respiratory rate for the patient. This is indicated by an icon 516 of a bell superimposed with an "X" symbol. The icon 516 indicates that the current respiratory rate of the patient is within the acceptable range. In a situation in which the respiratory rate for the patient is not within the acceptable level, the icon 516 can change to indicate an alarm state. For example, the "X" can disappear from the icon 516 and the icon 516 can light up or flash to indicate an alarm state. Additionally, the display device 504 can emit an audible alarm to alert nearby caregivers to an alarm state for the patient. In some implementations, other portions of the user interface 506 can flash or otherwise indicate an alarm state. For example, the displayed respiratory rate value 512 can flash when the patient's respiratory rate is outside of the acceptable range 514. In some implementations, the icon 516 (or other portions of the user interface 506) can flash at varying rates to indicate the severity of a particular alarm state. For example, the icon 516 can flash faster the further the patient's respiratory rate is from the acceptable range.

Figure 6:
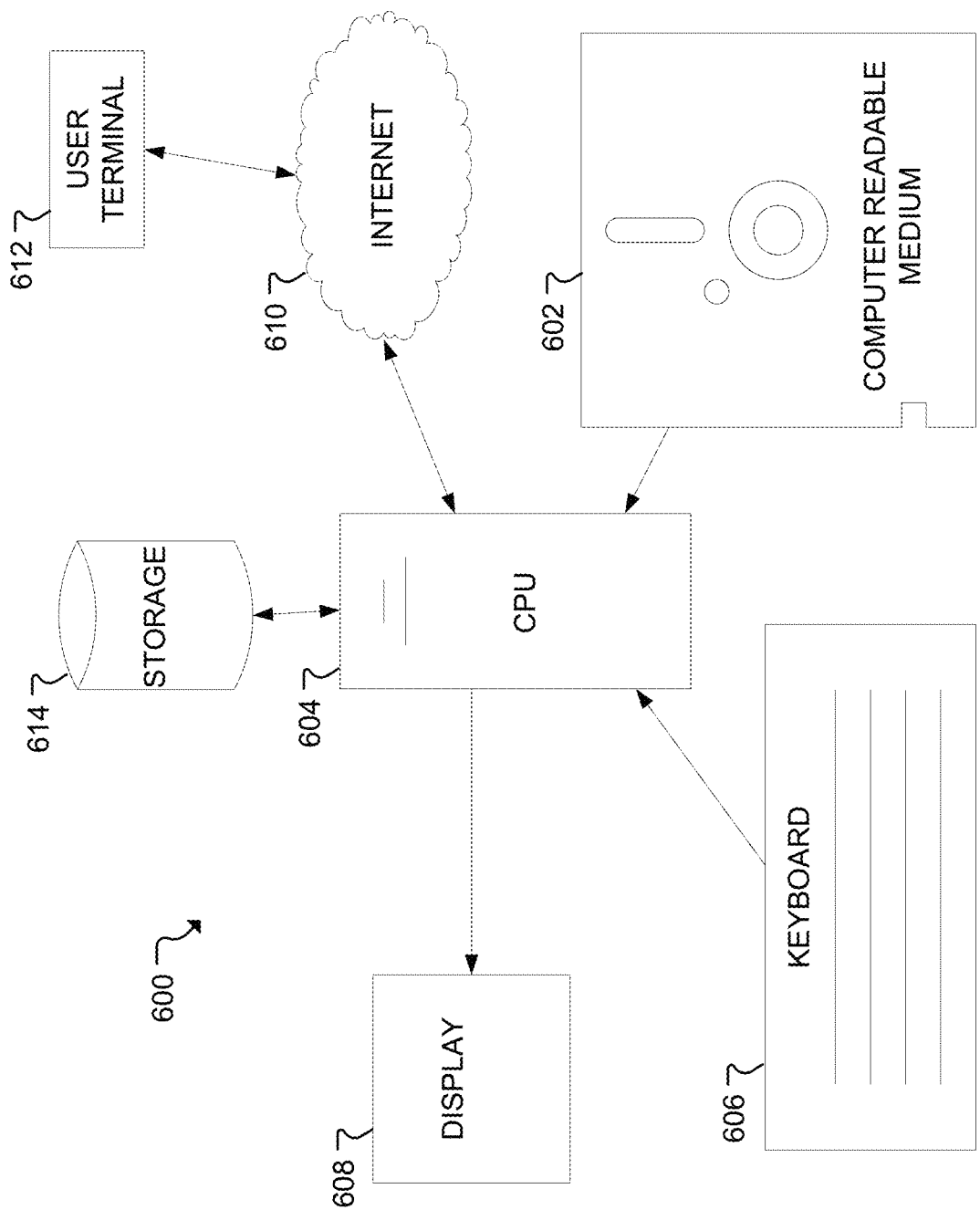
FIG. 6 is a block diagram showing an example of a computing system that may be used to implement a respiratory rate processing system.

FIG. 6 is a block diagram showing an example of a computing system 600 executing a computer program that implements the above-described operations, data structures, and/or programs contained on a computer readable medium 602, and executed by a central processing unit (CPU) 604. The CPU 604 may be an x86 series CPU or other CPU known in the art. Input to execute the program can, in some implementations, come by way of a keyboard 606. In some implementations, input to execute the program can come by way of a peripheral device such as a mouse, light pen, touch screen, touch pad, or any other input device known in the art. In some implementations, the described operations can be called by another program to execute and process oximetry data. Once processed, data processed using the above-described operations, data structures, and/or programs can be outputted to a display 608, or sent via an internet 610 or other wireless communications channel to another user terminal 612. In some implementations, the output can be placed into a database 614 or another database located off-site.

Figure 7:
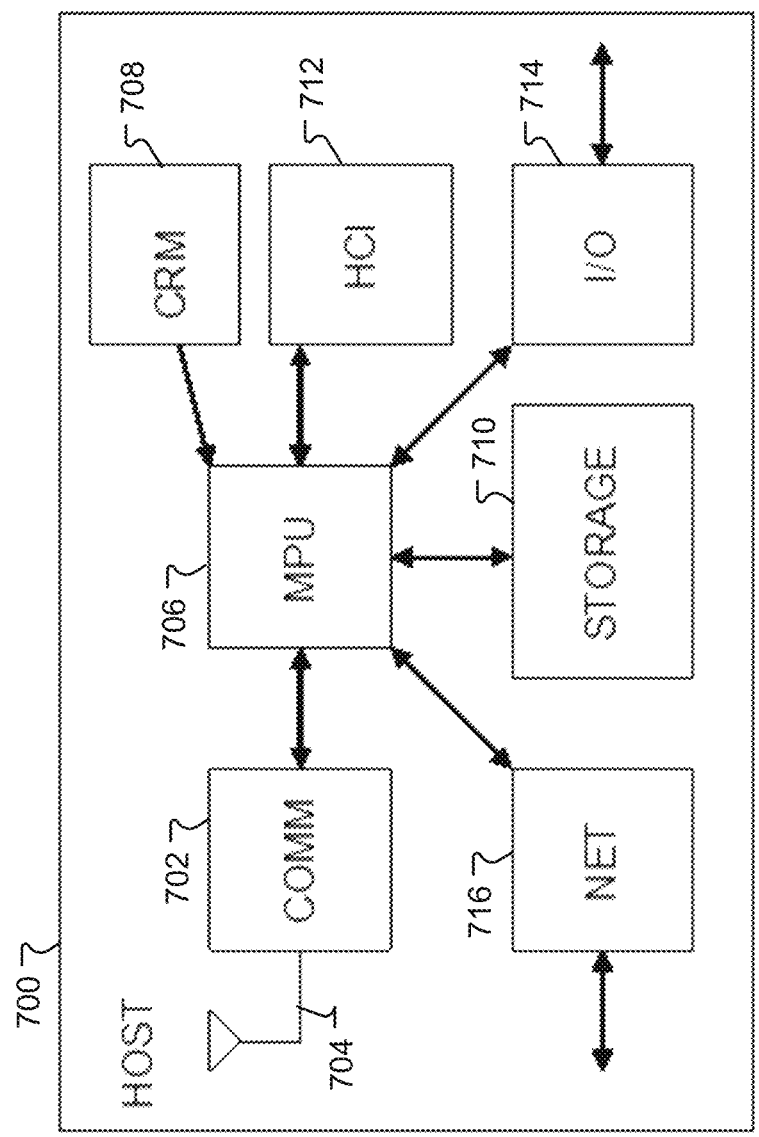
FIG. 7 is a block diagram showing an example of a computing system that depicts a host system that may be used to implement a respiratory rate processing system.

FIG. 7 is a block diagram showing an example of a computing system that depicts a host 700 which may, in some implementations, include a set of units or modules such as a communications module (COMM) 702 and associated communications link 704 for communicating with a patient worn sensor, a microprocessor unit (MPU) 706 including a computer readable medium (CRM) 708 containing a set of application instructions, an associated storage module 710 for storing patient data, a human-computer interface (HCI) 712 by which an operator (e.g., a physician, technician, or patient) may interact with the MPU 706 and which may include a visual display, auditory display, keyboard, mouse, touch screen, haptic device, or other means of interaction. The host 700 also includes an input/output (I/O) module 714 for generally connecting to, and communicating with, computer peripherals such as for example printers, scanners, and/or data acquisition or imaging equipment, and a network communications module (NET) 716 for communicating with other hosts on a computer network such as Ethernet and/or a wireless network, or WiFi.

The features described in this disclosure can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor, and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing context.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer area processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application specific integrated circuits). To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet. The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as Such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software or hardware product or packaged into multiple software or hardware products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A non-transitory computer readable storage medium encoded with a computer program, the program comprising instructions that when executed by one or more data processing apparatus cause the one or more data processing apparatus to perform operations comprising:
   receiving a signal corresponding to impedance across a patient's chest cavity;
   filtering the signal using one or more filters that reduce noise and center the signal around a zero baseline;
   adjusting an amplitude of the filtered signal based on a threshold value;
   separating the amplitude-adjusted signal into component signals, wherein each of the component signals represents a frequency-limited band;
   detecting a fractional phase transition of a component signal of the component signals;
   selecting a dominant component signal from the component signals based on amplitudes of the component signals at a time corresponding to the detected fractional phase transition;
   determining a frequency of the dominant component signal at the time corresponding to the detected fractional phase transition; and
   determining a respiratory rate of the patient based on the determined frequency.

2. The non-transitory computer readable storage medium of claim 1, wherein separating the amplitude-adjusted signal into the component signals comprises filtering the signal using a bank of bandpass filters.

3. The non-transitory computer readable storage medium of claim 1, wherein detecting the fractional phase transition of a component signal comprises detecting positive-going zero crossings, negative-going zero crossings, positive peaks, and negative peaks of the component signal.

4. The non-transitory computer readable storage medium of claim 1, wherein adjusting the amplitude of the filtered signal based on the threshold value comprises:
   determining the threshold value based on an average amplitude of the filtered signal; and
   clipping the filtered signal based on the threshold value.

5. The non-transitory computer readable storage medium of claim 1, wherein selecting the dominant component signal comprises:
   generating, at the detected fractional phase transition of the component signal, a data object containing values representing the time, the amplitude, and a phase corresponding to the component signal at the detected fractional phase transition; and
   selecting, as the dominant component signal, a component signal having a highest amplitude based on amplitude values contained in data objects generated for the component signals corresponding to the time of the detected fractional phase transition.

6. The non-transitory computer readable storage medium of claim 1, wherein determining the frequency of the dominant component signal is based upon determining time and phase differences between fractional phase transitions.

7. The non-transitory computer readable storage medium of claim 1, wherein determining the patient's respiratory rate comprises determining an average respiratory rate over a time period.

8. A computer-implemented method comprising:
   receiving a signal corresponding to impedance across a patient's chest cavity;
   filtering the signal using one or more filters that reduce noise and center the signal around a zero baseline;
   adjusting an amplitude of the filtered signal based on a threshold value;
   separating the amplitude-adjusted signal into component signals, wherein each of the component signals represents a frequency-limited band;
   detecting a fractional phase transition of a component signal of the component signals;

selecting a dominant component signal from the component signals based on amplitudes of the component signals at a time corresponding to the detected fractional phase transition;

determining a frequency of the dominant component signal at the time corresponding to the detected fractional phase transition; and determining a respiratory rate of the patient based on the determined frequency.

9. The computer-implemented method of claim 8, wherein separating the amplitude-adjusted signal into the component signals comprises filtering the signal using a bank of bandpass filters.

10. The computer-implemented method of claim 8, wherein detecting the fractional phase transition of a component signal comprises detecting positive-going zero crossings, negative-going zero crossings, positive peaks, and negative peaks of the component signal.

11. The computer-implemented method of claim 8, wherein adjusting the amplitude of the filtered signal based on the threshold value comprises:

determining the threshold value based on an average amplitude of the filtered signal;

and clipping the filtered signal based on the threshold value.

12. The computer-implemented method of claim 8, wherein selecting the dominant component signal comprises:

generating, at the detected fractional phase transition of the component signal, a data object containing values representing the time, the amplitude, and a phase corresponding to the component signal at the detected fractional phase transition; and selecting, as the dominant component signal, a component signal having a highest amplitude based on amplitude values contained in data objects generated for the component signals corresponding to the time of the detected fractional phase transition.

13. The computer-implemented method of claim 8, wherein determining the frequency of the dominant component signal is based upon determining time and phase differences between fractional phase transitions.

14. The computer-implemented method of claim 8, wherein determining the patient's respiratory rate comprises determining an average respiratory rate over a time period.

\* \* \* \* \*